United States Patent
Park et al.

(10) Patent No.: US 9,956,603 B2
(45) Date of Patent: May 1, 2018

(54) APPARATUS FOR PROCESSING SURFACE OF WORKPIECE

(71) Applicant: KOREA INSTITUTE OF MACHINERY & MATERIALS, Daejeon (KR)

(72) Inventors: Jong-Kweon Park, Daejeon (KR); Seung Kook Ro, Daejeon (KR); Sung Cheul Lee, Daejeon (KR); Byung-Sub Kim, Daejeon (KR); Kornel Ehmann, Evanston, IL (US)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 196 days.

(21) Appl. No.: 14/840,095

(22) Filed: Aug. 31, 2015

(65) Prior Publication Data
US 2017/0058999 A1 Mar. 2, 2017

(51) Int. Cl.
*B21G 1/08* (2006.01)
*B21B 27/02* (2006.01)
(Continued)

(52) U.S. Cl.
CPC .............. *B21G 1/08* (2013.01); *B21B 27/024* (2013.01); *B21C 51/005* (2013.01); *B21H 8/00* (2013.01);
(Continued)

(58) Field of Classification Search
CPC .. B21B 1/16; B21B 1/163; B21B 1/18; B21B 13/103; B21B 27/024; B21B 27/035;
(Continued)

(56) References Cited

U.S. PATENT DOCUMENTS 324,867 A * 8/1885 Meatyard .............. B21B 13/103
144/246.1
371,424 A * 10/1887 Clifford et al. ....... B21B 13/103
72/224
(Continued)

FOREIGN PATENT DOCUMENTS

JP 08-243602 9/1996
JP 2014-042949 3/2014
(Continued)

*Primary Examiner* — Edward Tolan
(74) *Attorney, Agent, or Firm* — LEX IP MEISTER, PLLC

(57) ABSTRACT

An apparatus for processing the surface of a workpiece includes: a first rotating body connected to a first rotating shaft and including a first protruding portion connected to a part of the outer circumference thereof; a second rotating body connected to a second rotating shaft and including a second protruding portion connected to a part of the outer circumference thereof; and a third rotating body connected to a third rotating shaft and including a third protruding portion connected to a part of the outer circumference thereof, wherein the first to third rotating shafts are in the same plane, a first angle between the first and second rotating shafts, a second angle between the first and third rotating shafts, and a third angle between the second and third rotating shafts are identical, outer circumferences of the first to third rotating shafts adjacent to one another form a pathway through which a workpiece can pass, and the size of the pathway is adjusted by moving the first rotating body.

11 Claims, 9 Drawing Sheets

(51) Int. Cl.
   *B21C 51/00*    (2006.01)
   *B21H 8/00*     (2006.01)
   *B44B 5/00*     (2006.01)
   *B21B 13/10*    (2006.01)
   *A61M 5/32*     (2006.01)

(52) U.S. Cl.
   CPC .......... *B44B 5/0009* (2013.01); *B44B 5/0061* (2013.01); *A61M 5/329* (2013.01); *B21B 13/103* (2013.01)

(58) Field of Classification Search
   CPC ......... B21B 31/20; B21B 31/22; B21B 1/085; B21B 13/08; B21B 13/10; B21D 15/02; B21D 17/04; B21C 51/005; B21G 1/08; B44B 5/0009
   See application file for complete search history.

(56) References Cited

U.S. PATENT DOCUMENTS

| | | | | |
|---|---|---|---|---|
| 3,186,206 A | * | 6/1965 | Gillberg | B21B 1/163 72/194 |
| 3,535,904 A | * | 10/1970 | Bindernagel | B21B 27/035 492/1 |
| 3,789,450 A | * | 2/1974 | Mozdenski | B44D 3/164 15/105 |
| 4,779,437 A | * | 10/1988 | Kubiak | B21D 53/262 101/22 |
| 5,953,948 A | * | 9/1999 | Isozaki | B21B 13/103 72/224 |
| 6,490,901 B2 | * | 12/2002 | Potthoff | B21B 13/103 72/224 |
| 8,113,027 B2 | * | 2/2012 | McDonald | B21H 1/20 148/641 |
| 2003/0136168 A1 | * | 7/2003 | Goto | B21B 13/103 72/224 |
| 2014/0124721 A1 | * | 5/2014 | Olsson | B21B 1/08 256/21 |

FOREIGN PATENT DOCUMENTS

| | | |
|---|---|---|
| KR | 10-2008-0105556 | 12/2008 |
| KR | 10-2011-0113037 | 10/2011 |

* cited by examiner

APPARATUS FOR PROCESSING SURFACE OF WORKPIECE

BACKGROUND OF THE INVENTION (a) Field of the Invention

The present invention relates to an apparatus for processing the surface of a workpiece, and more particularly, to an apparatus for processing the surface of a workpiece which processes the surface of a cylindrical member.

(b) Description of the Related Art

Drugs may be injected into a human body using fine needles so that the drugs are efficiently absorbed into the body. Further, examination equipment is mounted at the end of a needle-like cylindrical member and injected into the body in order to conduct a physical checkup.

In the course of injecting a fine needle or the like into a human body, ultrasonic instrument may be used to check and adjust the position of the needle.

However, such fine needles are often not shown on the ultrasonic instrument because they are so tiny, often making it difficult to accurately inject these needles into the human body.

The above information disclosed in this Background section is only for enhancement of understanding of the background of the invention and therefore it may contain information that does not form the prior art that is already known in this country to a person of ordinary skill in the art.

SUMMARY OF THE INVENTION

Based upon the technical background discussed above, the present invention has been made in an effort to provide an apparatus for processing the surface of a workpiece, which forms a certain pattern on the outer circumference of a cylindrical member like a needle.

An exemplary embodiment of the present invention provides an apparatus for processing the surface of a workpiece, the apparatus including: a first rotating body connected to a first rotating shaft and including a first protruding portion connected to a part of the outer circumference thereof; a second rotating body connected to a second rotating shaft and including a second protruding portion connected to a part of the outer circumference thereof; and a third rotating body connected to a third rotating shaft and including a third protruding portion connected to a part of the outer circumference thereof, wherein the first to third rotating shafts are in the same plane, a first angle between the first and second rotating shafts, a second angle between the first and third rotating shafts, and a third angle between the second and third rotating shafts are identical, outer circumferences of the first to third rotating shafts adjacent to one another form a pathway through which a workpiece can pass, and the size of the pathway is adjusted by moving the first rotating body.

The first to third protruding portions may be replaceably connected to the first to third rotating bodies, respectively.

The first to third protruding portions may be partially received in the first to third rotating bodies, respectively.

The first to third rotating bodies may have a cylindrical shape.

A recess may be formed on the outer circumferences of the first to third rotating bodies.

The first to third protruding portions may come into contact with the outer circumference of the workpiece.

The first to third angles may be 60 degrees.

The apparatus may include: a pair of first gears connected to the first rotating shaft; a second gear connected to the second rotating shaft and meshing with one of the pair of first gears; and a third gear connected to the third rotating shaft and meshing with the other first gear.

The first rotating body may be positioned between the pair of first gears.

The first to third gears may be bevel gears.

The apparatus may further include: a driving shaft connected to the first rotating shaft; and a driving portion connected to the driving shaft and rotating the driving shaft.

First to third bearings may be connected to the first to third rotating shafts, respectively.

The apparatus may further include: a housing to which the second and third rotating shafts are rotatably secured; and a sliding portion connected to the first rotating shaft and being slidable along a guide portion formed on the housing.

According to the above-described workpiece surface processing apparatus, a certain pattern may be formed on the outer circumference of a fine cylindrical member.

Moreover, patterns of various shapes may be formed on the outer circumference of a member since the protruding portions can be replaced with ones of various shapes.

Additionally, a cost decrease and a reduction in processing time can be achieved simply by replacing a damaged or abraded protruding portion only.

DETAILED DESCRIPTION OF THE EMBODIMENTS

Figure 1:
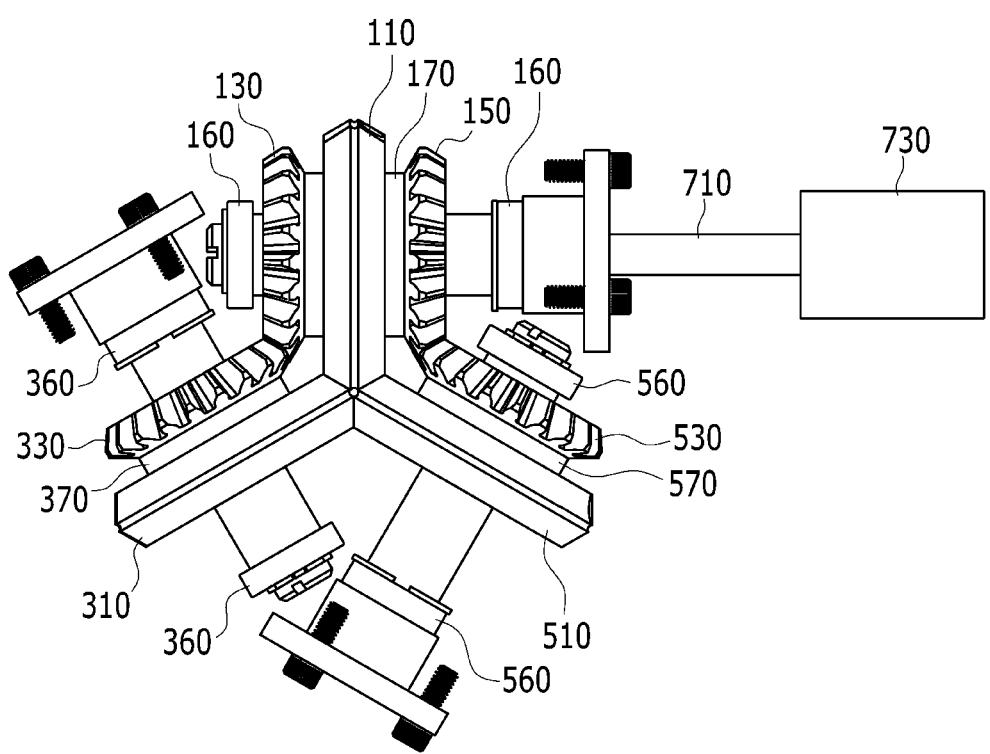
FIG. 1 is a schematic plane view of an apparatus for processing the surface of a workpiece according to one exemplary embodiment of the present invention.

Hereinafter, the present invention will be described in detail with reference to the accompanying drawings so that a person of ordinary skill in the art may easily perform the present invention. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

In the drawings, the sizes and thicknesses of the components are merely shown for convenience of explanation, and therefore the present invention is not necessarily limited to the illustrations described and shown herein.

Further, unless explicitly described to the contrary, the word "include" and variations such as "includes" or "including" will be understood to imply the inclusion of stated elements but not the exclusion of any other elements. In addition, in the entire specification, "on" means being positioned on or under an object part and does not necessarily mean being positioned on the object part based on a gravity direction.

Hereinafter, an apparatus for processing the surface of a workpiece according to an exemplary embodiment of the present invention will be described with reference to FIGS. 1 and 2.

Figure 2:
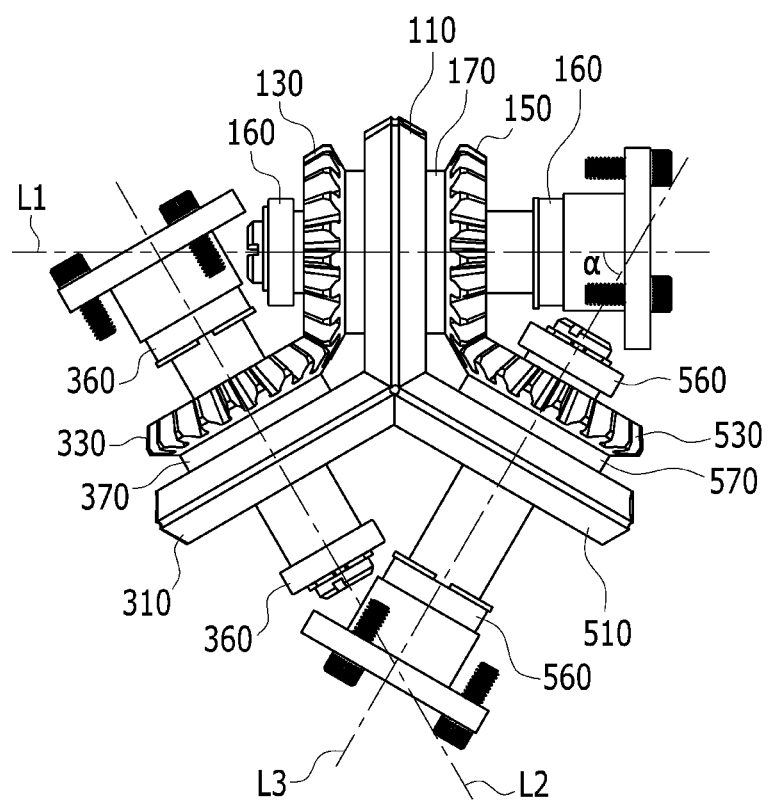
FIG. 2 is a view showing the connection relationship between first to third rotating shafts.

FIG. 1 is a schematic plane view of an apparatus for processing the surface of a workpiece according to one exemplary embodiment of the present invention, and FIG. 2 is a view showing the connection relationship between first to third rotating shafts.

Referring to FIG. 1 and FIG. 2, the workpiece surface processing apparatus according to one exemplary embodiment of the present invention includes a first rotating body 110, a first protruding portion 190, a first rotating shaft 170, a second rotating body 310, a second protruding portion 390, a second rotating shaft 370, a third rotating body 510, a third protruding portion 590, and a third rotating shaft 570.

The workpiece surface processing apparatus according this exemplary embodiment may form a certain pattern on the outer circumference of a workpiece, such as a needle, a pipe, a tubular member, etc. In this case, a pathway formed by the first to third rotating bodies 110, 310, and 510 of the apparatus may be regulated, so that workpieces of various diameters can pass through the pathway.

The first rotating shaft 170 is a bar-like member, to which the first rotating body 110 and first gears 130 and 150 to be described later are connected. The first rotating shaft 170 may rotate with the first rotating body 110, first gears 130 and 150, and so on.

The first rotating body 110 is connected to the first rotating shaft 170. That is, the first rotating body 110 may rotate with the first rotating shaft 170.

The first rotating body 110 may have a cylindrical shape. A recess may be formed on the outer circumference of the first rotating body 110. The recess is formed along the outer circumference of the first rotating body 110 to form a circular shape.

Figure 6:
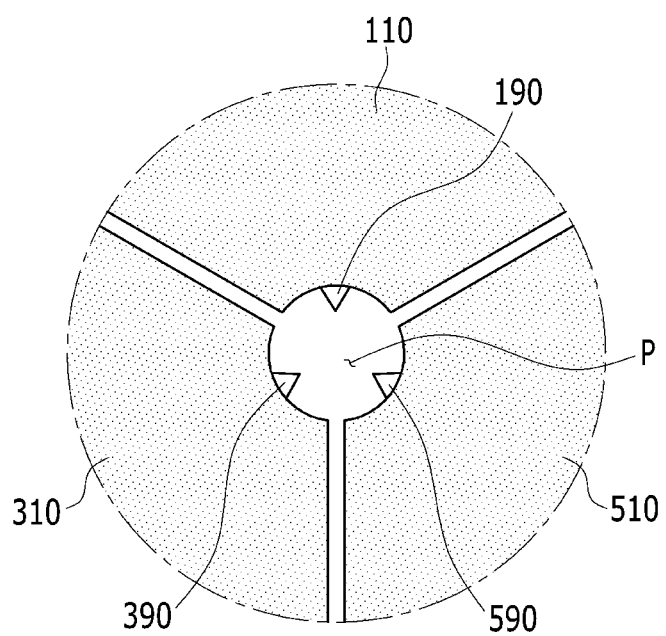
FIGS. 6, 7, and 8 are views showing a process of securing a workpiece between protruding portions.

A recess identical to that of the first rotating body 110 is formed on the outer circumferences of the second and third rotating bodies 310 and 510 to be described later. As shown in FIG. 6, a pathway P through which a workpiece can pass may be formed by the outer circumferences of the first to third rotating bodies 110, 310, and 510.

The center of the outer circumference of the first rotating body 110 may be protruded. For example, the center of the outer circumference where the recess is formed may be protruded farther than the edge of the outer circumference.

A first bearing 160 is connected to the first rotating shaft 170. A pair of first bearings 160 may be connected to the first rotating shaft 170. The first bearing 160 rotatably supports the first rotating shaft 170.

A first bearing 160 may be positioned on each side of the first rotating body 110.

The first bearings 160 may be ball bearings.

In the present exemplary embodiment, a pair of first gears 130 and 150 are connected to the first rotating shaft 170. The pair of first gears 130 and 150 may rotate with the first rotating shaft 170. The pair of first gears 130 and 150 may be positioned on either side of the first rotating body 110. The pair of first gears 130 and 150 may be positioned between the first rotating body 110 and the first bearings 160.

The pair of first gears 130 and 150 mesh with second and third gears 330 and 530 to be described later, respectively.

That is, one of the first gears (130) meshes with the second gear 330, and the other first gear (150) meshes with the third gear 530.

Thus, when the pair of first gears 130 and 150 rotate, the second gear 330 and the third gear 530 also rotate. As a consequence, when the first rotating shaft 170 rotates, the second and third rotating shafts 370 and 570 to be described later can also rotate.

The pair of first gears 130 and 150 may be bevel gears. Thus, torque may be transmitted among the first to third rotating shafts 170, 370, and 570 which are not parallel to one another.

Figure 4:
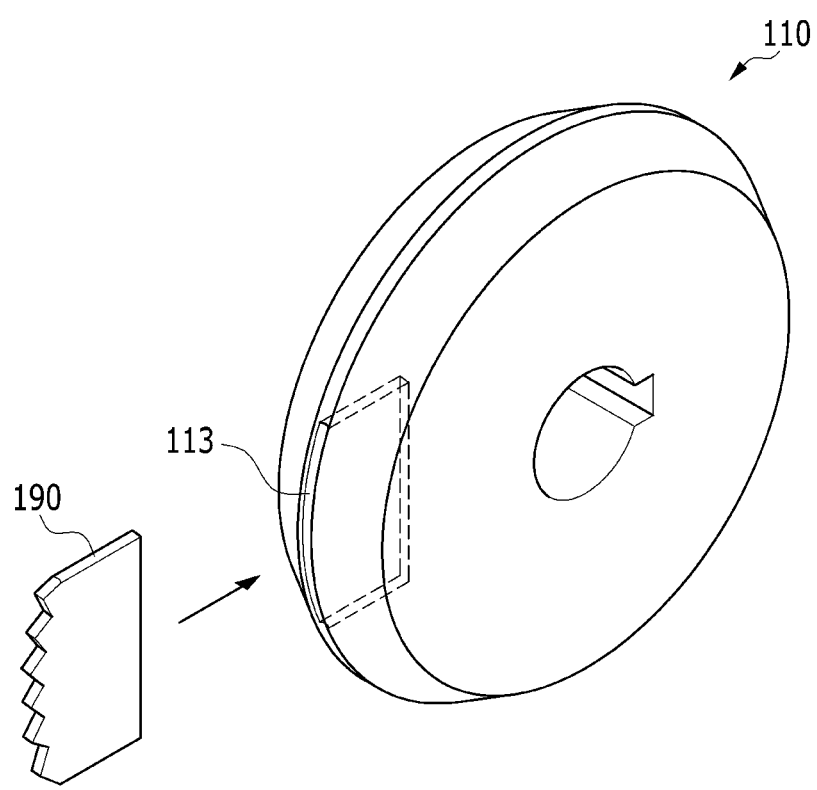
FIG. 4 and FIG. 5 are views showing a process of connecting a rotating body and a protruding portion.
Figure 5:
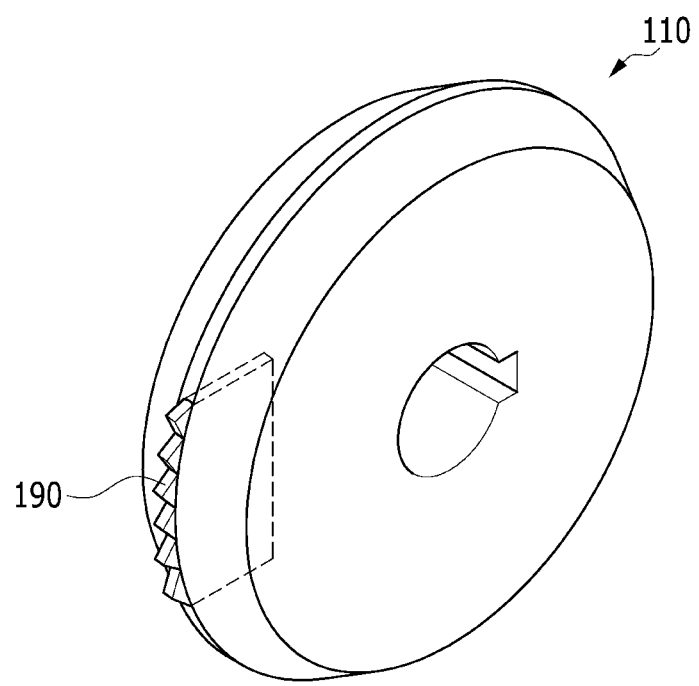

Referring to FIG. 4 and FIG. 5, in the present exemplary embodiment, a first protruding portion 190 is connected to the first rotating body 110. The first protruding portion 190 is positioned within the recess on the outer circumference of the first rotating body 110.

The first protruding portion 190 may be received in a receiving portion 113 formed in the first rotating body 110. The remaining part of the first protruding portion 190, except projections, is received in the first rotating body 110.

According to the present exemplary embodiment, the first protruding portion 190 is replaceable. The first protruding portion 190 may be replaced depending on the shape and size of a pattern S to be formed on the outer circumference of a workpiece N. That is, the first protruding portion 190 may be replaced with others of various shapes and sizes.

Meanwhile, in case of damage or abrasion of the projections of the first protruding portion 190, it may be replaced with a new one. That is, if the projections are formed integrally on the first rotating body 110, the entire first rotating body needs to be replaced in case of damage or abrasion of the projections, thus causing a cost increase. However, in the present exemplary embodiment, the apparatus may become operable again simply by only replacing the first protruding portion 190 in case of damage or abrasion, thereby decreasing costs and reducing processing time.

Referring to FIG. 4 and FIG. 5, only one first protruding portion 190 may be disposed on the outer circumference of the first rotating body 110. However, the present invention is not limited thereto, and a plurality of first protruding portions 190 may be disposed on the outer circumference of the first rotating body 110. The plurality of first protruding portions 190 may be spaced apart at regular intervals on the outer circumference of the first rotating body 110.

Referring again to FIG. 1, a driving shaft 710 and a driving portion 730 are sequentially connected to the first rotating shaft 170. A torque generated by the driving portion 730 is transmitted to the first rotating shaft 170 through the driving shaft 710. That is, when the driving portion 730 goes into operation, the first rotating body 110 also rotates as the first rotating shaft 710 rotates.

A connecting member (not shown) may be positioned between the first rotating shaft 170 and the driving shaft 730. Even if the first rotating shaft 170 and the driving shaft 730 are not in the same straight line, the connecting member may transmit torque from the driving shaft 730 to the first rotating shaft 170.

The second rotating shaft 370 is a bar-like member to which the second rotating body 310, the second gear 330, and so on may be connected. The second rotating shaft 370 may rotate with the second rotating body 310, the second gear 330, and so on.

Referring to FIG. 2, the second rotating shaft 370 crosses the first rotating shaft 170 at a first angle. The angle between a first virtual line L1 passing the first rotating shaft 170 and a second virtual line L2 passing the second rotating shaft 370 may be the first angle. The first angle may be 60 degrees.

The second rotating body 310 is connected to the second rotating shaft 370. That is, the second rotating body 310 may rotate with the second rotating shaft 370.

Like the above-described first rotating body 110, the second rotating body 310 may have a cylindrical shape. A recess is formed on the outer circumference of the second rotating body 310. The recess is formed along the second rotating body 310 to form a circular shape.

That is, a recess identical to that of the first rotating body 110 is formed on the outer circumference of the second rotating body 310.

The center of the outer circumference of the second rotating body 310 may be protruded. For example, the center of the outer circumference where the recess is formed may be protruded farther than the edge of the outer circumference.

A second bearing 360 is connected to the second rotating shaft 370. A pair of second bearings 360 may be connected to the second rotating shaft 370. The second bearing 360 rotatably supports the second rotating shaft 370.

A second bearing 360 may be positioned on each side of the second rotating body 310. The second bearings 360 may be ball bearings.

In the present exemplary embodiment, the second gear 330 is connected to the second rotating shaft 370. The second gear 330 may rotate with the second rotating shaft 370. The second gear 330 may be positioned on one side of the second rotating shaft 370. In this case, the second gear 330 is fixed at a position where it can mesh with the adjacent first gear 130.

As described above, the second gear 330 meshes with the above-described first gear 130.

Thus, when the pair of first gears 130 and 150 rotate, the second gear 330 also rotates. As a consequence, when the first rotating shaft 170 rotates, the second rotating shaft 370 can also rotate with the first gears 130 and 150 and the second gear 330 meshing with one another.

Like the first gears 130 and 150, the second gear 330 may be a bevel gear. Thus, torque may be transmitted between the first and second rotating shafts 170 and 370 which are not parallel to each another.

In the present exemplary embodiment, like the first protruding portion 190, a second protruding portion 390 is connected to the second rotating body 310. The second protruding portion 390 is positioned within the recess on the outer circumference of the second rotating body 310.

The second protruding portion 390 may be received in a receiving portion (not shown) formed in the second rotating body 310. The remaining part of the second protruding portion 390, except projections, is received in the second rotating body 310.

According to the present exemplary embodiment, the second protruding portion 390 is replaceable. The second protruding portion 390 may be replaced depending on the shape and size of a pattern S to be formed on the outer circumference of a workpiece N. The second protruding portion 390 may be replaced with others of various shapes and sizes.

That is, in case of damage or abrasion of the projections of the second protruding portion 390, it may be replaced with a new one. If the projections are formed integrally on the second rotating body 310, the entire second rotating body needs to be replaced in case of damage or abrasion of the projections, thus causing a cost increase. That is, in the present exemplary embodiment, the apparatus may become operable again by simply replacing the second protruding portion 390 in case of damage or abrasion, thereby decreasing costs and reducing processing time.

Like the first protruding portion 190, only one second protruding portion 390 may be disposed on the outer circumference of the second rotating body 310. However, the present invention is not limited thereto, and a plurality of second protruding portions 390 may be disposed on the outer circumference of the second rotating body 310. The plurality of second protruding portions 390 may be spaced apart at regular intervals on the outer circumference of the second rotating body 310.

The third rotating shaft 570 is a bar-like member, to which the third rotating body 510, the third gear 530, and so on may be connected. The third rotating shaft 570 may rotate with the third rotating body 510, the third gear 330, and so on.

Referring to FIG. 2, the third rotating shaft 570 crosses the first rotating shaft 170 at a second angle. The angle between a third virtual line L3 passing the third rotating shaft 570 and the first virtual line L1 passing the first rotating shaft 170 may be the second angle. The second angle may be 60 degrees.

Also, the third rotating shaft 570 crosses the second rotating shaft 370 at a third angle. The angle between the third virtual line L3 passing the third rotating shaft 570 and the second virtual line L2 passing the second rotating shaft 370 may be the third angle. The third angle may be 60 degrees.

That is, according to the present exemplary embodiment, the first to third rotating shafts 170, 370, and 570 are in the same plane, and the first to third angles among the first to third rotating shafts 170, 370, and 570 are all the same. As a consequence, the first to third angles are all 60 degrees.

The third rotating body 510 is connected to the third rotating shaft 570. That is, the third rotating body 510 may rotate with the third rotating shaft 570.

Like the above-described first and second rotating bodies 110 and 310, the third rotating body 510 may have a cylindrical shape. A recess is formed on the outer circumference of the third rotating body 510. The recess is formed along the second rotating body 510 to form a circular shape.

That is, a recess identical to that of the first rotating body 110 is formed on the outer circumference of the third rotating body 510.

The center of the outer circumference of the second rotating body 510 may be protruded. For example, the center of the outer circumference where the recess is formed may be protruded farther than the edge of the outer circumference.

A third bearing 560 is connected to the third rotating shaft 570. A pair of third bearings 560 may be connected to the third rotating shaft 570. The third bearing 560 rotatably supports the third rotating shaft 570.

A third bearing 560 may be positioned on each side of the third rotating body 510. The third bearings 560 may be ball bearings.

In the present exemplary embodiment, the third gear 530 is connected to the third rotating shaft 570. The third gear 530 may rotate with the third rotating shaft 570. The third gear 530 may be positioned on one side of the third rotating shaft 570. In this case, the third gear 530 is fixed at a position where it can mesh with the adjacent first gear 150.

As described above, the third gear 530 meshes with the above-described first gear 150.

Thus, when the pair of first gears 130 and 150 rotate, the third gear 530 also rotates. As a consequence, when the first rotating shaft 170 rotates, the third rotating shaft 570 also can rotate with the first gears 130 and 150 and the third gear 530 meshing with one another. According to the present exemplary embodiment, when the first rotating shaft 170 connected to the driving shaft 710 rotates, the second rotating shaft 370 and the third rotating shaft 570 may rotate simultaneously by the first gears 130 and 150, the second gear 330, and the third gear 530 meshing with one another.

The third gear 530 may be a bevel gear. Thus, torque may be transmitted between the first and third rotating shafts 170 and 570 which are not parallel to each another.

In the present exemplary embodiment, like the first protruding portion 190 and the second protruding portion 390, the third protruding portion 590 is connected to the third rotating body 510. The third protruding portion 590 is positioned within the recess on the outer circumference of the third rotating body 510.

Figure 9:
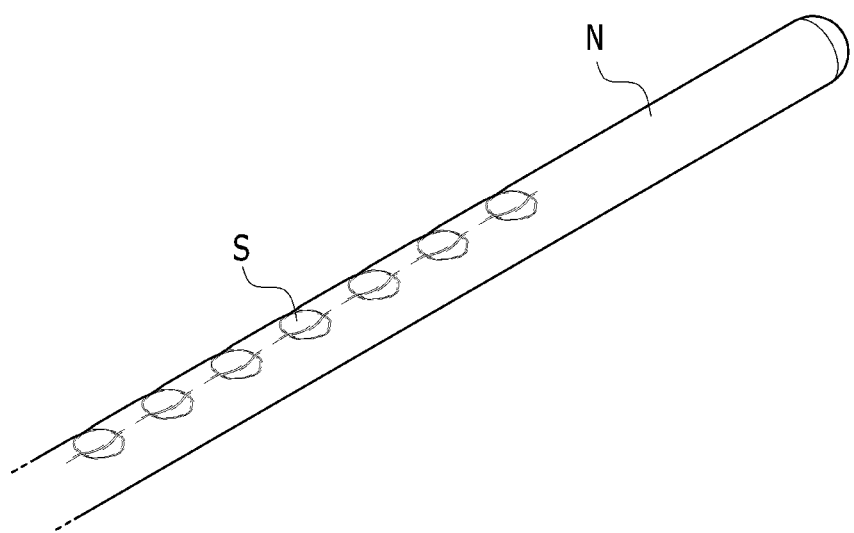
FIG. 9 is a view of depressions formed on the outer circumference of a workpiece by the workpiece surface processing apparatus.

The first to third protruding portions 190, 390, and 590 form a certain pattern S on the outer circumference of a workpiece N. Referring to FIG. 9, a pattern S is formed on the outer circumference of a workpiece N, corresponding to the shape of the first to third protruding portions 190, 390, and 590.

The third protruding portion 590 may be received in a receiving portion (not shown) formed in the third rotating body 510. The remaining part of the third protruding portion 590, except projections, is received in the third rotating body 510.

According to the present exemplary embodiment, the third protruding portion 590 is replaceable. The third protruding portion 590 may be replaced depending on the shape and size of a pattern S to be formed on the outer circumference of the workpiece N. That is, the third protruding portion 590 may be replaced with others of various shapes and sizes.

In other words, in case of damage or abrasion of the projections of the third protruding portion 590, it may be replaced with a new one. If the projections are formed integrally on the third rotating body 510, the entire second rotating body needs to be replaced in case of damage or abrasion of the projections, thus causing a cost increase. However, in the present exemplary embodiment, the apparatus may become operable again by simply replacing the third protruding portion 590 in case of damage or abrasion, thereby decreasing costs and reducing processing time.

Like the first and second protruding portions 190 and 390, only one third protruding portion 590 may be disposed on the outer circumference of the third rotating body 510. However, the present invention is not limited thereto, and a plurality of third protruding portions 590 may be disposed on the outer circumference of the third rotating body 510. The plurality of third protruding portions 590 may be spaced apart at regular intervals on the outer circumference of the third rotating body 510.

Figure 3:
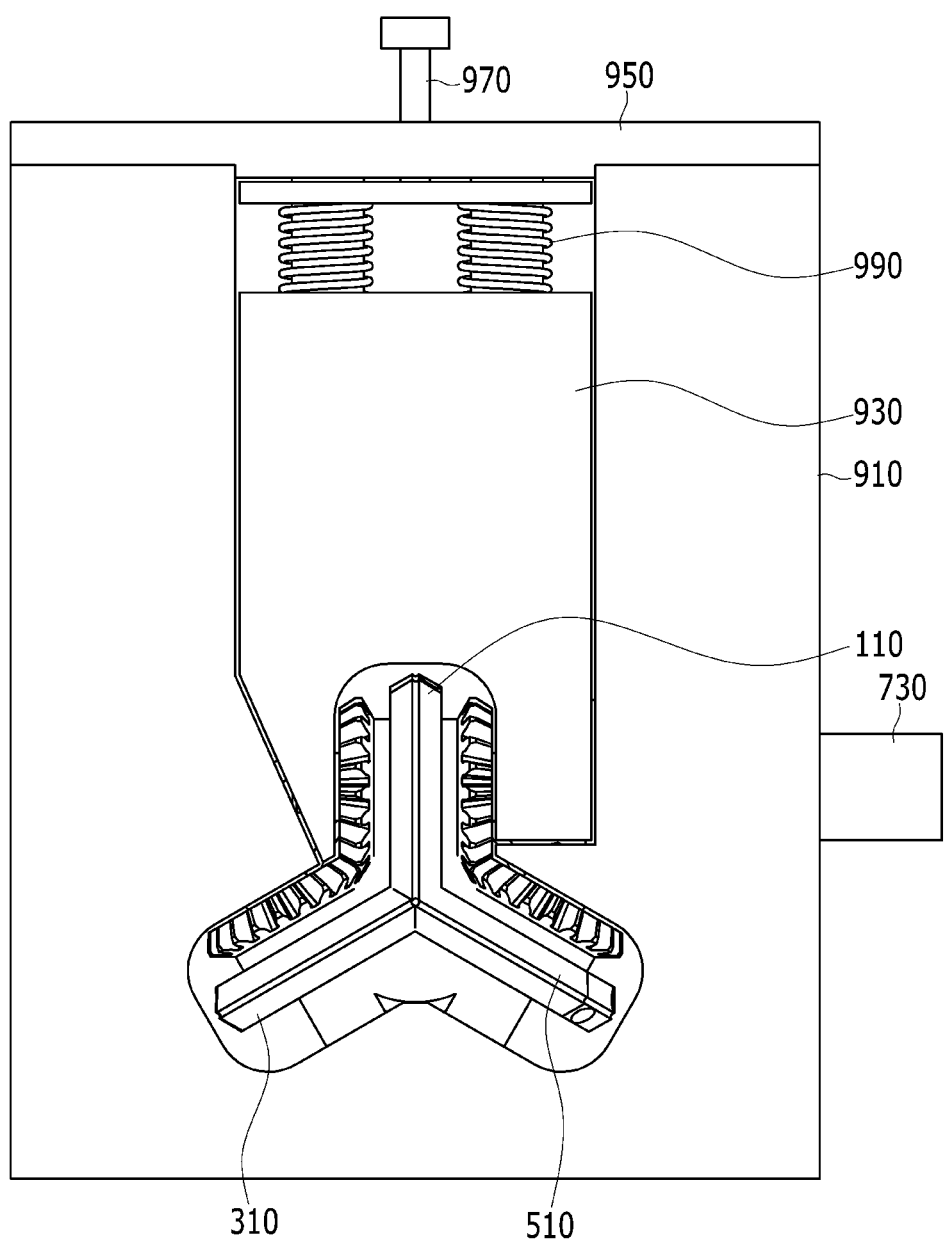
FIG. 3 is a view of a housing being connected to the workpiece surface processing apparatus according to the present exemplary embodiment.

Referring to FIG. 3, the second and third rotating shafts 370 and 570 are connected to a housing 910. The second rotating shaft 370 and the third rotating shaft 570 may be rotatably connected to the housing 910.

According to the present exemplary embodiment, the first rotating shaft 170 may move in one direction. As shown in FIG. 3, the first rotating shaft 170 may move vertically along a sliding portion 930.

The sliding portion 930 moves vertically along a U-shaped guide portion formed on the housing 910. That is, the first rotating shaft 170 may move vertically along with the sliding portion 930.

The position of the sliding portion 930 is adjusted by an adjustment portion 970 penetrating a fixed plate 950 located over the housing 910. For example, the sliding portion 930 may be moved upward or downward by turning the adjustment portion 970.

According to the present exemplary embodiment, the first to third rotating bodies 110, 310, and 510 may form a pathway through which a workpiece N can pass. The workpiece N that passes through the pathway may vary in diameter. To pass workpieces N of various diameters therethrough, the workpiece surface processing apparatus according to this exemplary embodiment may change the size of the pathway.

Figure 7:
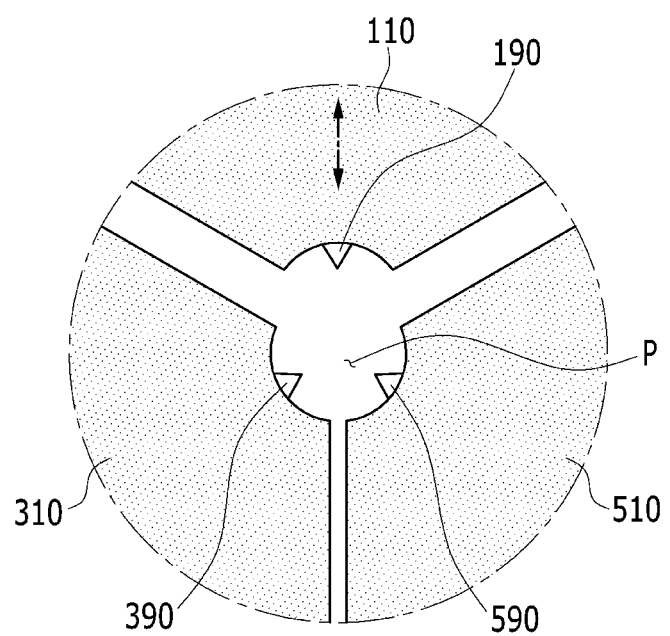
Figure 8:
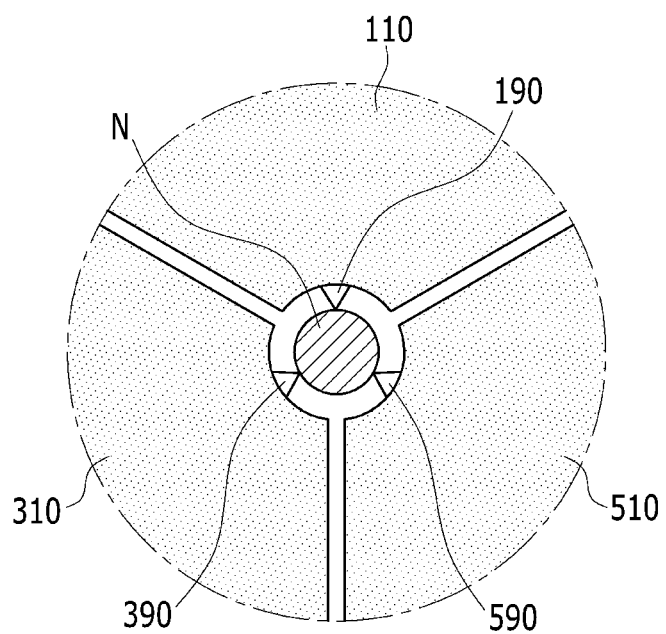

Referring to FIGS. 6 to 8, the first rotating body 110 may move vertically. If the position of the first rotating body 110 is changed, the size of the pathway P may be changed. For example, if the first rotating body 110 moves upward, the size of the pathway P becomes larger. On the contrary, if the first rotating body 110 moves downward, the size of the pathway P becomes smaller.

The workpiece surface processing apparatus according to one exemplary embodiment of the present invention is capable of processing the outer circumferences of workpieces N of various sizes by adjusting the size of a pathway formed by the first to third rotating bodies 110, 310, and 510. Moreover, since the first to third protruding portions 190, 390, and 590 are replaceable, a cost decrease and reduction in processing time can be achieved by simply replacing a damaged or abraded protruding portion.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

| <Description of symbols> | | | |
|---|---|---|---|
| 110 | first rotating body | 130, 150 | first gear |
| 160 | first bearing | 170 | first rotating shaft |
| 190 | first protruding portion | 310 | second rotating body |
| 330 | second gear | 360 | second bearing |
| 370 | second rotating shaft | 390 | second protruding portion |
| 510 | third rotating body | 530 | third gear |
| 560 | third bearing | 570 | third rotating shaft |

What is claimed is:

1. An apparatus for processing the surface of a workpiece, the apparatus comprising:
    a first rotating body connected to a first rotating shaft and comprising a first protruding portion connected to a part of an outer circumference thereof;
    a second rotating body connected to a second rotating shaft and comprising a second protruding portion connected to a part of an outer circumference thereof; and
    a third rotating body connected to a third rotating shaft and comprising a third protruding portion connected to a part of an outer circumference thereof,
    wherein the first to third rotating shafts are in the same plane,
    a first angle between the first and second rotating shafts, a second angle between the first and third rotating shafts, and a third angle between the second and third rotating shafts are identical,
    a recess is formed on the outer circumferences of the first to third rotating bodies, respectively, the recesses of the first to third rotating bodies are disposed adjacently to one another and form together a pathway through which a workpiece can pass, the size of the pathway is adjusted by moving the first rotating body, the first to third protruding portions are positioned within the recesses of the first to third rotating bodies and come into contact with an outer circumference of the workpiece in the recess, and there is a gap between the workpiece and the pathway when the workpiece passes through the pathway.

2. The apparatus of claim 1, wherein the first to third protruding portions are replaceably connected to the first to third rotating bodies, respectively.

3. The apparatus of claim 2, wherein the first to third protruding portions are partially received in the first to third rotating bodies, respectively.

4. The apparatus of claim 1, wherein the first to third rotating bodies have a cylindrical shape.

5. The apparatus of claim 1, wherein the first to third angles are degrees.

6. The apparatus of claim 1, further comprising:
a pair of first gears connected to the first rotating shaft;
a second gear connected to the second rotating shaft and meshing with one of the pair of first gears; and
a third gear connected to the third rotating shaft and meshing with the other first gear.

7. The apparatus of claim 6, wherein the first rotating body is positioned between the pair of first gears.

8. The apparatus of claim 6, wherein the first to third gears are bevel gears.

9. The apparatus of claim 1, further comprising:
a driving shaft connected to the first rotating shaft; and
a driving portion connected to the driving shaft and rotating the driving shaft.

10. The apparatus of claim 1, wherein first to third bearings are connected to the first to third rotating shafts, respectively.

11. The apparatus of claim 1, further comprising:
a housing to which the second and third rotating shafts are rotatably secured; and
a sliding portion connected to the first rotating shaft and being slidable along a guide portion formed on the housing.

* * * * *